(12) United States Patent
Anderson, Jr. et al.

(10) Patent No.: US 11,369,781 B2
(45) Date of Patent: Jun. 28, 2022

(54) FLUIDIC DISPENSING APPARATUS AND ASSOCIATED FLUID DISPENSING CARTRIDGE

(71) Applicant: FUNAI ELECTRIC CO., LTD., Osaka (JP)

(72) Inventors: James D. Anderson, Jr., Harrodsburg, KY (US); Michael A. Marra, III, Lexington, KY (US)

(73) Assignee: FUNAI ELECTRIC CO., LTD., Osaka (JP)

( * ) Notice: Subject to any disclaimer, the term of this patent is extended or adjusted under 35 U.S.C. 154(b) by 769 days.

(21) Appl. No.: 16/286,060

(22) Filed: Feb. 26, 2019

(65) Prior Publication Data

US 2020/0269027 A1 Aug. 27, 2020

(51) Int. Cl.
| | |
|---|---|
| *A61M 31/00* | (2006.01) |
| *A61K 9/00* | (2006.01) |
| *B41J 2/165* | (2006.01) |
| *B41J 2/175* | (2006.01) |
| *A61M 11/04* | (2006.01) |
| *A61M 15/06* | (2006.01) |

(52) U.S. Cl.
CPC ......... *A61M 31/007* (2013.01); *A61K 9/0043* (2013.01); *A61K 9/0046* (2013.01); *B41J 2/16505* (2013.01); *B41J 2/17513* (2013.01); *B41J 2/17553* (2013.01); *B41J 2/17563* (2013.01); *A61M 11/042* (2014.02); *A61M 15/06* (2013.01)

(58) Field of Classification Search
CPC .... B41J 2/17513; B41J 2/17553; B41J 2/175; B41J 2/01; B41J 2/001
USPC ............................................................ 347/87
See application file for complete search history.

(56) References Cited

U.S. PATENT DOCUMENTS

| | | | |
|---|---|---|---|
| 7,322,349 | B2 | 1/2008 | Power |
| 8,794,231 | B2 | 8/2014 | Thorens et al. |
| 9,986,767 | B2 | 6/2018 | Batista et al. |
| 2002/0122098 | A1* | 9/2002 | Sekiya ................... B41J 2/1752 347/50 |
| 2006/0077217 | A1 | 4/2006 | Yang et al. |
| 2016/0219938 | A1 | 8/2016 | Mamoun et al. |
| 2016/0255880 | A1 | 9/2016 | Dubief |
| 2017/0190174 | A1 | 7/2017 | Dodd et al. |
| 2018/0020736 | A1 | 1/2018 | Silvestrini et al. |
| 2018/0116281 | A1 | 5/2018 | Anderson, Jr. |

(Continued)

FOREIGN PATENT DOCUMENTS

| | | |
|---|---|---|
| CA | 2924114 A1 | 3/2015 |
| CN | 105640761 A | 6/2016 |

(Continued)

*Primary Examiner* — Kristal Feggins
*Assistant Examiner* — Alexander D Shenderov
(74) *Attorney, Agent, or Firm* — Dinsmore & Shohl LLP (57) ABSTRACT

A fluid dispensing cartridge includes a housing body having a proximal end wall, a distal end wall, a fluid chamber, and a hollow throat portion. The fluid chamber is in fluid communication with the hollow throat portion. The proximal end wall provides a proximal termination of the fluid chamber and the distal end wall provides a distal termination of the hollow throat portion. A plurality of electrical contacts face proximally from the proximal end wall. The fluid dispensing cartridge includes a fluid jetting chip that has a plurality of fluid jetting nozzles.

19 Claims, 8 Drawing Sheets

(56) References Cited

U.S. PATENT DOCUMENTS

2018/0192700 A1 7/2018 Fraser
2018/0199627 A1 7/2018 Bowen et al.
2018/0303168 A1 10/2018 DePiano et al.

FOREIGN PATENT DOCUMENTS

EP 1768858 A2 4/2007
FR 2929861 A1 10/2009

* cited by examiner

FLUIDIC DISPENSING APPARATUS AND ASSOCIATED FLUID DISPENSING CARTRIDGE

CROSS-REFERENCE TO RELATED APPLICATIONS

This application is related to U.S. patent application Ser. No. 16/286,060.

BACKGROUND OF THE INVENTION

1. Field of the Invention

The present invention relates to fluidic dispensing devices, and, more particularly, to a fluidic dispensing apparatus and associated fluid dispensing cartridge.

2. Description of the Related Art

One type of fluid jetting cartridge is an ink jet cartridge for use with an ink jet printer, which includes a mechanism that scans the cartridge over a print medium, such as paper. In such a design, the size of the nozzle array is enlarged to cover a swath height on the print medium. However, such an ink jet printer design is not suitable for a personal application of a fluid, such as in a medication dispenser (e.g., a nasal spray applicator) or a personal writing instrument (e.g., a handheld ink pen). In part, this is because the ink jet cartridge is not configured to be hand-manipulated and controlled. In addition, for medication dispensing applications, an ink jet cartridge is not suitable in size or configuration to be inserted into a small orifice of a person, such as a nostril or ear canal.

What is needed in the art is a fluidic dispensing apparatus and associated fluid dispensing cartridge, which is configured to be hand-manipulated and controlled, and is suitable in size and configuration for a particular application for personal use.

SUMMARY OF THE INVENTION

The present invention provides a fluidic dispensing apparatus and associated fluid dispensing cartridge, which is configured to be hand-manipulated and controlled, and is suitable in size and configuration for a particular application for personal use.

The invention in one form is directed to a fluid dispensing cartridge that includes a housing body having a proximal end wall, a distal end wall, a fluid chamber, and a hollow throat portion. The fluid chamber is in fluid communication with the hollow throat portion. The proximal end wall provides a proximal termination of the fluid chamber and the distal end wall provides a distal termination of the hollow throat portion. A plurality of electrical contacts face proximally from the proximal end wall. A fluid jetting chip has a plurality of fluid jetting nozzles. In one embodiment, for example, the fluid jetting chip may be located on, and attached to, the distal end wall.

The invention in another form is directed to a fluidic dispensing apparatus that includes a handle and a fluid dispensing cartridge. The handle has a controller portion and a cartridge housing. The controller portion has a first plurality of electrical contacts. The housing is removably engaged with the controller portion. The cartridge housing has a distal opening. The fluid dispensing cartridge is positioned in the cartridge housing. The fluid dispensing cartridge has a proximal end wall and a hollow throat portion that extends distally through the distal opening. The hollow throat portion has a distal end wall that mounts a fluid jetting chip. The fluid jetting chip has a plurality of fluid jetting nozzles, and has a second plurality of electrical contacts that face proximally from the proximal end wall for engagement with the first plurality of electrical contacts of the controller portion.

One advantage of the invention, in general, is that the fluidic dispensing apparatus with the associated fluid dispensing cartridge may be hand-manipulated and controlled, with one hand, so as to position and operate the jetting chip for jetting a fluid toward a target area.

Another advantage of the present invention, in a medicinal application, for example, is that a portion of the apparatus is sized and shaped to fit through a small orifice and into a small passageway, such as a nostril or ear canal, so as to position the jetting chip as near the target area as possible.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
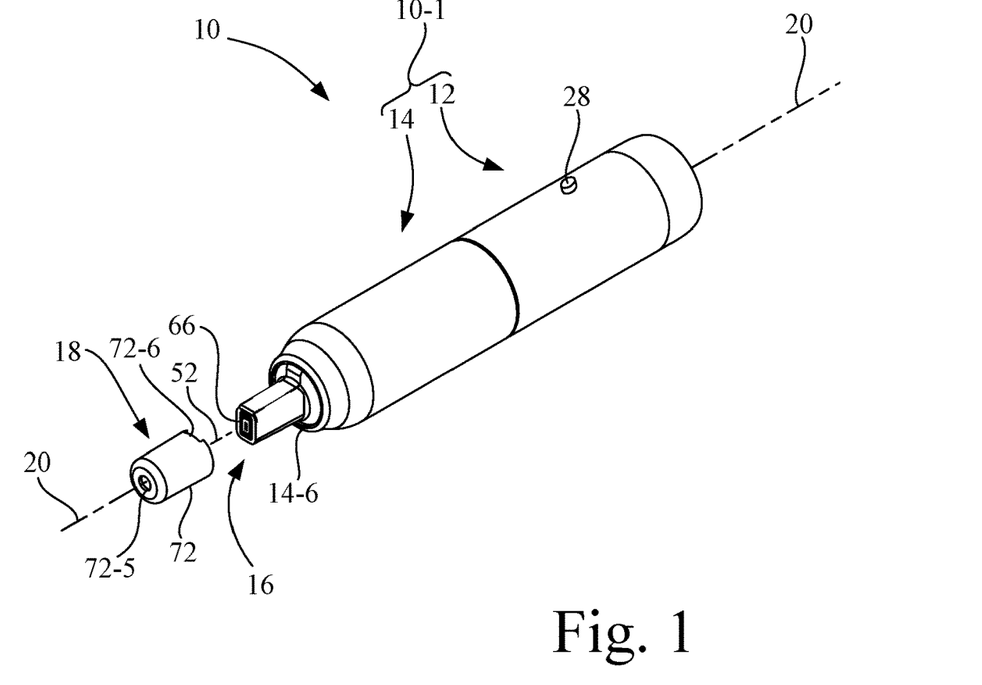
FIG. 1 is a fluidic dispensing apparatus in accordance with an embodiment of the present invention.

Referring now to the drawings, and more particularly to FIGS. 1-4, there is shown a fluidic dispensing apparatus 10, which includes a controller portion 12, a cartridge housing 14, a fluid dispensing cartridge 16, and a cartridge throat cover 18 arranged along a longitudinal axis 20. Controller portion 12 and cartridge housing 14 in combination form a handle 10-1 of fluidic dispensing apparatus 10. As shown in FIG. 1, cartridge housing 14 is removably engaged, i.e., connected, with controller portion 12. In the present invention, cartridge throat cover 18 is optional.

Figure 2:
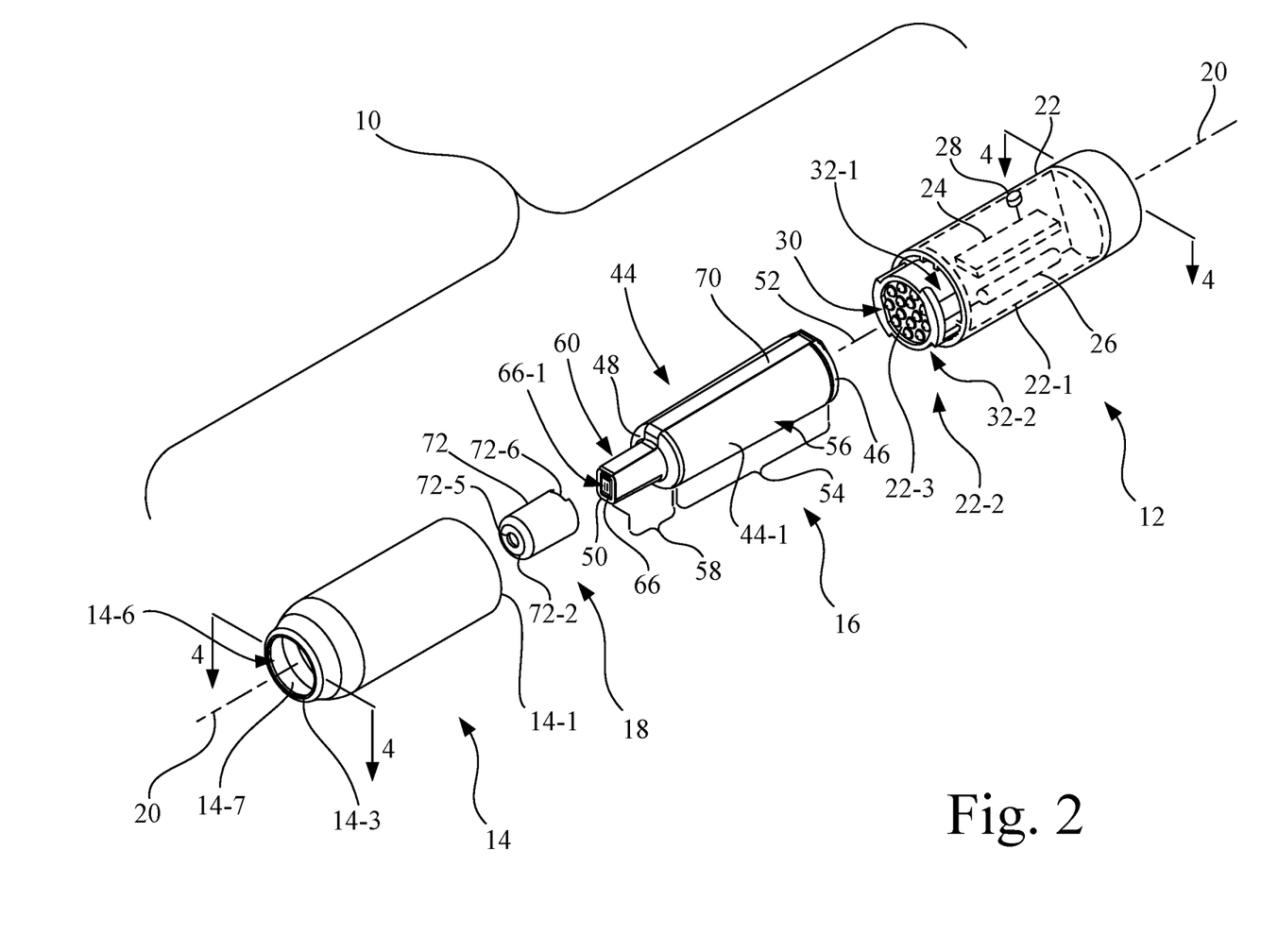
FIG. 2 is an exploded predominantly rear perspective view of the fluidic dispensing apparatus of FIG. 1, depicting a hollow throat portion of the fluid dispensing cartridge having a fluid jetting chip and depicting an electrical connection arrangement of the controller portion of the fluidic dispensing apparatus.
Figure 4:
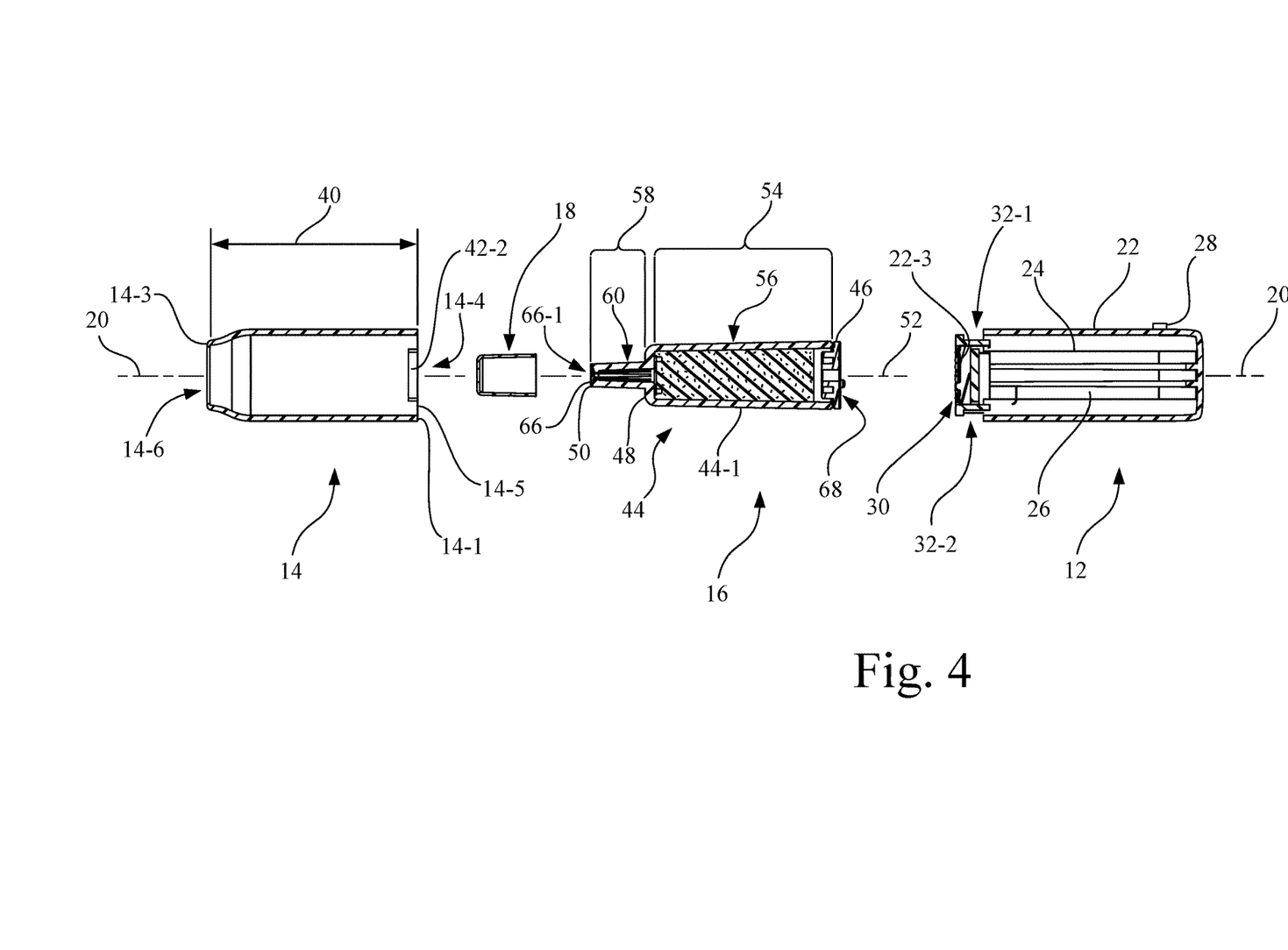
FIG. 4 is a side section view of the fluidic dispensing apparatus of FIGS. 1-3 taken along plane 4-4 of FIG. 2.

Referring to FIGS. 2 and 4, controller portion 12 includes a controller housing 22, a control circuit 24, a battery 26, an actuator button 28, and a plurality of electrical contacts 30.

Figure 5:
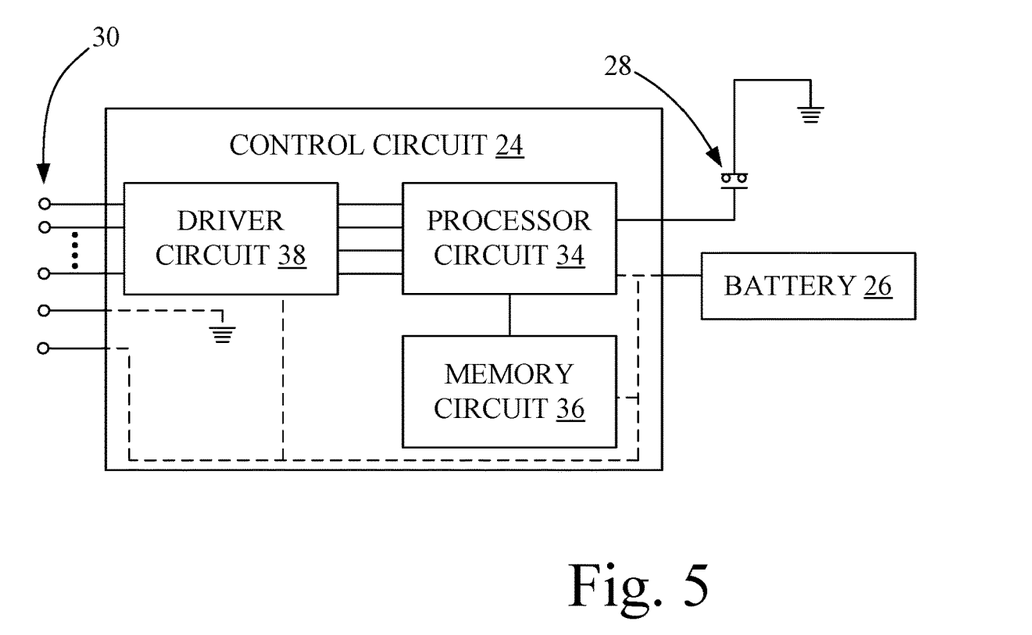
FIG. 5 is a block diagram of a control circuit of the controller portion of the fluidic dispensing apparatus of FIG. 1.

Controller housing 22 includes a cavity 22-1 that contains control circuit 24 and battery 26. In the present embodiment, an exterior of controller housing 22 is generally cylindrical. Referring also to FIG. 5, battery 26 is connected to control circuit 24, and in turn supplies electrical power to all electrical components of control circuit 24, and to fluid dispensing cartridge 16 via control circuit 24.

Figure 3:
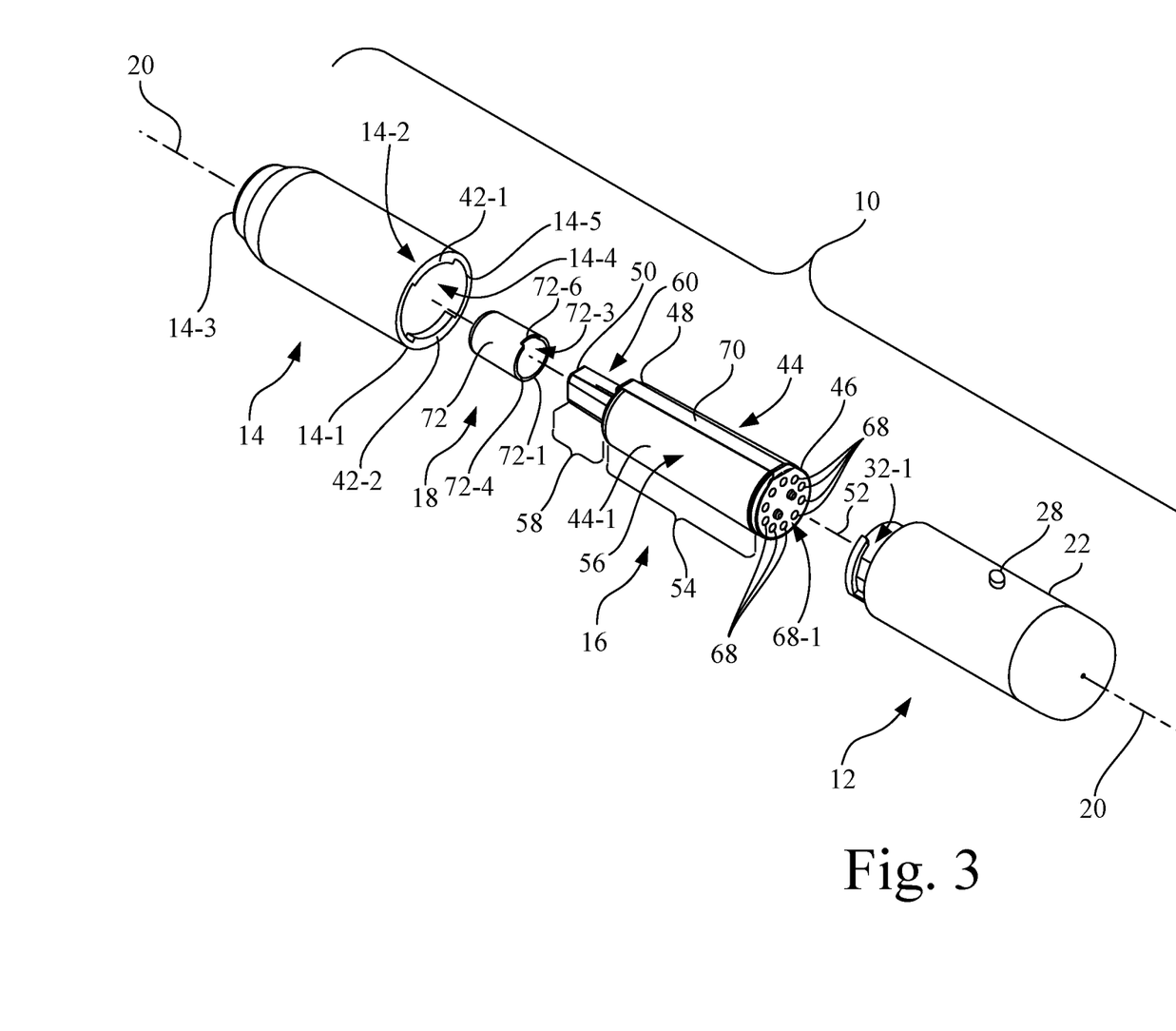
FIG. 3 is an exploded predominantly front perspective view of the fluidic dispensing apparatus of FIG. 1, depicting the hollow throat portion of the fluid dispensing cartridge and depicting a proximal electrical connection arrangement of the fluid dispensing cartridge.

As shown in FIGS. 2-4, in the present embodiment, controller housing 22 has a coupling portion 22-2 and a distal end surface 22-3.

Coupling portion 22-2 is configured for detachable attachment to a corresponding portion of cartridge housing 14. Coupling portion 22-2 may be, for example, radially opposed slots 32-1, 32-2 that rotationally receive a corresponding pair of radially opposed tabs 42-1, 42-2 of cartridge housing 14. In the present embodiment, coupling portion 22-2 of controller housing 22 is configured for quarter-turn detachable attachment to cartridge housing 14.

Referring to FIGS. 2 and 4, the plurality of electrical contacts 30 of controller portion 12 is exposed at, and may alternatively project from, distal end surface 22-3 of controller housing 22.

Referring also to FIG. 5, control circuit 24 includes a processor circuit 34, a memory circuit 36, and a driver circuit 38. Control circuit 24 may be formed as one or more Application Specific Integrated Circuits (ASIC).

Processor circuit 34 may have one or more programmable microprocessors and associated circuitry, such as an input/output interface, clock, buffers, memory, etc. Memory circuit 36 is communicatively coupled to processor circuit 34, e.g., via a bus circuit, and may include volatile memory circuits, such as random access memory (RAM), and non-volatile memory circuits, such as read only memory (ROM), electronically erasable programmable ROM (EEPROM), NOR flash memory, NAND flash memory, etc.

Processor circuit 34 of control circuit 24 is electrically connected to battery 26, and is electrically and communicatively connected to actuator button 28, memory circuit 36, and driver circuit 38. Driver circuit 38 is electrically connected to the plurality of electrical contacts 30 of controller portion 12.

Processor circuit 34 of control circuit 24 is configured via software and/or firmware to operate fluid dispensing cartridge 16 (see also FIGS. 1-4) for jetting a fluid contained in fluid dispensing cartridge 16. In particular, when a user depresses actuator button 28, actuator button 28 supplies an input signal to processor circuit 34. In turn, processor circuit 34 executes control signals to generate cartridge control signals. The cartridge control signals are supplied by processor circuit 34 to driver circuit 38. Driver circuit 38 conditions the cartridge control signals (e.g., through impedance matching, voltage amplification, current amplification, etc.) as needed to be compatible with the electrical requirements of fluid dispensing cartridge 16, and supplies the conditioned cartridge control signals to respective electrical contacts of the plurality of electrical contacts 30.

Control circuit 24 may also supply power and ground connections to fluid dispensing cartridge 16 via respective electrical contacts of the plurality of electrical contacts 30. The plurality of electrical contacts 30 supply the conditioned cartridge control signals, and power and ground, at a voltage level and/or current level suitable for the electrical jetting circuitry of fluid dispensing cartridge 16.

Referring again to FIGS. 2-4, cartridge housing 14 includes a proximal end 14-1, a coupling portion 14-2, a distal end 14-3, a chamber 14-4, a proximal opening 14-5, a distal opening 14-6, and an interior tapered annular surface 14-7. Chamber 14-4 extends between proximal end 14-1 and distal end 14-3 to define proximal opening 14-5 and distal opening 14-6. Each of chamber 14-4 and proximal opening 14-5 has a cross-sectional area, e.g., diameter, selected to axially receive fluid dispensing cartridge 16.

Interior tapered annular surface 14-7 is located a distance 40 from proximal end 14-1. Interior tapered annular surface 14-7 generally transitions longitudinally from the larger cross-sectional area, e.g., diameter, of chamber 14-4 to the relatively smaller cross-sectional area, e.g., diameter, of distal opening 14-6. Interior tapered annular surface 14-7 defines a stop within chamber 14-4 to limit an extent of a lengthwise portion of fluid dispensing cartridge 16 that can be received in chamber 14-4. In operation, fluid dispensing cartridge 16 is axially received into chamber 14-4 of cartridge housing 14 to a depth defined by interior tapered annular surface 14-7. Also, in the present embodiment, interior tapered annular surface 14-7 will tend to radially center fluid dispensing cartridge 16 on longitudinal axis 20.

Coupling portion 14-2 of cartridge housing 14 is configured for detachable attachment to coupling portion 22-2 of controller housing 22. Coupling portion 14-2 may include, for example, the pair of radially opposed tabs 42-1, 42-2 that are sized and shaped to axially and rotationally engage the radially opposed slots 32-1, 32-2 of controller housing 22. In the present embodiment, coupling portion 22-2 of controller housing 22 is configured for quarter-turn detachable attachment to coupling portion 14-2 of cartridge housing 14. Each of radially opposed tabs 42-1, 42-2 is inwardly-facing, i.e., extends toward longitudinal axis 20.

Also referring to FIG. 1, when coupling portion 14-2 of cartridge housing 14 is attached to coupling portion 22-2 of controller housing 22, fluid dispensing cartridge 16 is in a state of compression between distal end surface 22-3 of controller housing 22 and interior tapered annular surface 14-7 of cartridge housing 14, such that fluid dispensing cartridge 16 is axially and radially restrained in chamber 14-4 of cartridge housing 14. Stated differently, in the present embodiment, fluid dispensing cartridge 16 is axially and radially restrained in fluidic dispensing apparatus 10 by the combined effect of interior tapered annular surface 14-7 of cartridge housing 14 and distal end surface 22-3 of controller housing 22.

Referring to FIGS. 2-4, fluid dispensing cartridge 16 includes a housing body 44 having a proximal end wall 46, an intermediate wall 48, a distal end wall 50, and a central longitudinal axis 52. Housing body 44 is a unitary structure, and has an exterior surface 44-1. When fluid dispensing cartridge 16 is installed in handle 10-1, central longitudinal axis 52 of fluid dispensing cartridge 16 lies on, and is coincident with, longitudinal axis 20 of fluidic dispensing apparatus 10.

Figure 6A:
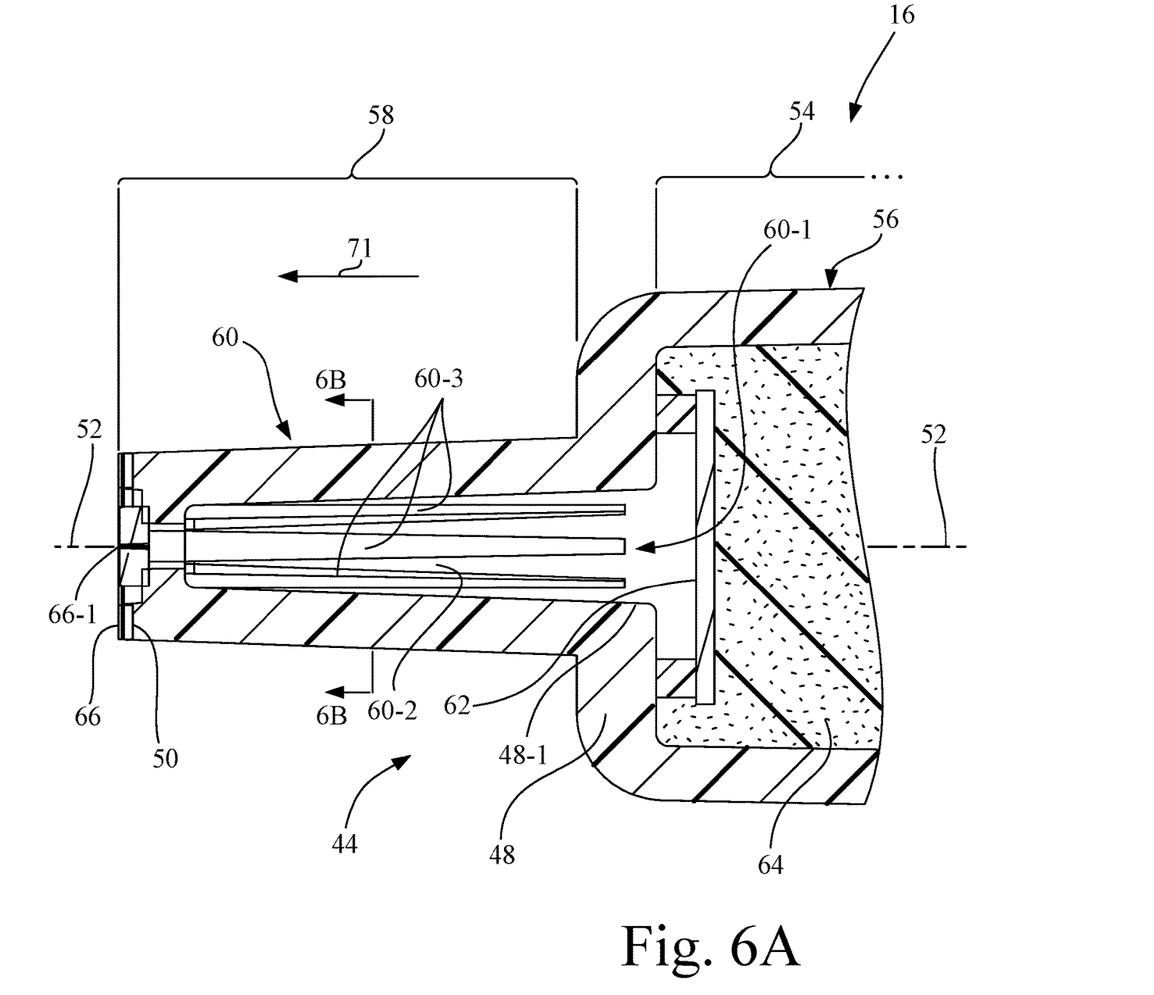
FIG. 6A is an enlarged portion of the side section view of FIG. 4, showing in greater detail the hollow throat portion of the fluid dispensing cartridge of the fluidic dispensing apparatus of FIGS. 1-4.

Proximal end wall 46 has a first surface area and distal end wall 50 has a second surface area, wherein the first surface area of proximal end wall 46 is greater than the second surface area of distal end wall 50. Intermediate wall 48 is located between, and is spaced from, proximal end wall 46 and distal end wall 50 along central longitudinal axis 52. A body region 54 between proximal end wall 46 and intermediate wall 48 defines a fluid chamber 56. A body region 58 between intermediate wall 48 and distal end wall 50 defines a hollow throat portion 60. Proximal end wall 46 provides a proximal termination of fluid chamber 56 and distal end wall 50 provides a distal termination of hollow throat portion 60. As shown in FIG. 6A with respect to FIG. 4, intermediate wall 48 has an opening 48-1 that facilitates fluid communication between fluid chamber 56 and hollow throat portion 60.

To effect assembly of fluidic dispensing apparatus 10, as depicted in FIG. 1, from the unassembled state depicted in FIGS. 2-4, fluid dispensing cartridge 16 is positioned in cartridge housing 14, prior to cartridge housing 14 being connected to controller portion 12. When fluid dispensing cartridge 16 is installed in cartridge housing 14, hollow throat portion 60 of fluid dispensing cartridge 16 extends distally through distal opening 14-6 of cartridge housing 14. Cartridge housing 14 is then connected to controller portion 12, which in turn establishes electrical connections between controller portion 12 and fluid dispensing cartridge 16.

Fluid chamber 56 has a first cross-sectional area perpendicular to central longitudinal axis 52, and hollow throat portion 60 has a second cross-sectional area perpendicular to the central longitudinal axis 52, wherein the first cross-sectional area is greater than the second cross-sectional area throughout the longitudinal extent of each of fluid chamber 56 and hollow throat portion 60. In the present embodiment, fluid chamber 56 is cylindrical in shape. In the present embodiment, a longitudinal extent of each of fluid chamber 56 and hollow throat portion 60 is along the central longitudinal axis 52.

Referring to FIG. 6A with respect to FIG. 4, a filter member 62 is located inside the housing body 44, and is positioned to cover opening 48-1 in intermediate wall 48 to separate fluid chamber 56 from hollow throat portion 60. Filter member 62 is porous, and in one embodiment is in the form of a mesh screen, e.g., a stainless steel mesh screen. Filter member 62 is connected to the intermediate wall 48, e.g., by heat staking, welding, adhesive, etc.

An absorbent body 64, such as a foam or felt body, is located in and substantially fills fluid chamber 56. Absorbent body 64 contains a fluid that is to be ejected, i.e., jetted, from fluid dispensing cartridge 16.

During assembly of fluid dispensing cartridge 16, filter member 62 and absorbent body 64 are installed in fluid chamber 56, and thereafter, proximal end wall 46 (also sometimes referred to as a lid) of housing body 44 is attached, e.g., ultrasonically welded, in sealing engagement to body region 54 of housing body 44.

Referring to FIGS. 2, 4, and 6A, fluid dispensing cartridge 16 includes a fluid jetting chip 66 that is located on, and is attached to, distal end wall 50 of housing body 44. In the present embodiment, a longitudinal extent of each of fluid chamber 56 and hollow throat portion 60 of housing body 44 is along the central longitudinal axis 52, and a center of each of fluid chamber 56, hollow throat portion 60, and fluid jetting chip 66 is located on central longitudinal axis 52.

Fluid jetting chip 66 is configured as a plate-like structure having a planar extent formed generally as a nozzle plate layer and a silicon layer, as is well known in the art. The nozzle plate layer of fluid jetting chip 66 includes a plurality of fluid jetting nozzles 66-1, such as for example, two to twenty fluid jetting nozzles. Associated with each of the plurality of fluid jetting nozzles 66-1, at the silicon layer of fluid jetting chip 66, is an ejection mechanism, such as a respective electrical heater (thermal) or piezoelectric (electromechanical) device that is individually associated with a respective fluid jetting nozzle of the plurality of fluid jetting nozzles 66-1. The general operation of such a fluid jetting chip is known in the micro-fluid ejection arts, such as in ink jet printing.

Referring also to FIG. 3, fluid dispensing cartridge 16 includes a plurality of electrical contacts 68 that is accessible at, and face proximally from, e.g., project proximally from, proximal end wall 46 of housing body 44. In the present embodiment, each of a center of proximal end wall 46 from which the plurality of electrical contacts 68 face proximally, and a center of fluid jetting chip 66 mounted to distal end wall 50, is located on central longitudinal axis 52.

The plurality of electrical contacts 68 are distributed on proximal end wall 46, with the plurality of electrical contacts 68 being spaced from one another and electrically insulated from one another. In the present embodiment, at least a portion of the plurality of electrical contacts 68 is arranged in a circular pattern 68-1 at proximal end wall 46. It is contemplated that a different circular distribution pattern of the plurality of electrical contacts 68 may be made in the form of a concentric circular pattern. Also, it is contemplated that other distribution patterns, such as polygonal, may be used as an alternative to the circular distribution pattern.

Referring to FIGS. 2-4, a circuit trace 70, such as a flexible tab circuit having a plurality of insulated conductors, is electrically connected to the plurality of electrical contacts 68 that face proximally from proximal end wall 46 of housing body 44, and is electrically connected to the fluid jetting chip 66 at distal end wall 50 of housing body 44, so as to establish electrical communication between the plurality of electrical contacts 68 and the plurality of jetting nozzles 66-1 of fluid jetting chip 66. As such, circuit trace 70 extends from proximal end wall 46 to distal end wall 50 along exterior surface 44-1 of housing body 44. Circuit trace 70 lies on and follows the contour of the longitudinal extent of exterior surface 44-1 of housing body 44, including body region 54 having fluid chamber 56 and body region 58 having hollow throat portion 60. Circuit trace 70 is attached to exterior surface 44-1 of housing body 44, such as by adhesive or heat staking.

Figure 6B:
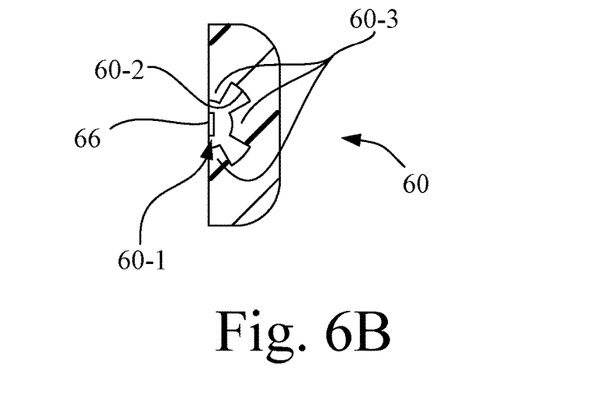
FIG. 6B is a section of the section view of FIG. 6B, taken along line 6B-6B of FIG. 6A, showing an axial view of the elongate protrusions in the fluid channel of the hollow throat portion of the fluid dispensing cartridge.

Referring to FIGS. 4, 6A and 6B, hollow throat portion 60 includes a fluid channel 60-1 having a length that defines a separation distance between the fluid jetting chip 66 and the filter member 62. Stated differently, hollow throat portion 60 defines fluid channel 60-1 as having a length that, in part, defines a separation distance between fluid jetting chip 66 and the plurality of electrical contacts 68.

In some applications, the amount of fluid to be jetted dictates a larger container size for fluid chamber 56 of body region 54, but requires that distal end wall 50 and fluid jetting chip 66 have a relatively small area, and requires that hollow throat portion 60 have a length sufficient, so as to position fluid jetting chip 66 within an orifice (e.g., ear canal or nostril) at the desired application site. As in the present embodiment, hollow throat portion 60 of fluid dispensing cartridge 16 is extended in length and with distal end wall 50 being made only large enough to house and mount fluid jetting chip 66. This, however, increases the volume of fluid that is accumulated distal to filter member 62, which is considered to be non-deliverable, and thus wasted, fluid. By adding ribs or other features internal to fluid channel 60-1, i.e., the filter-to-jetting chip fluid path, the volume of non-deliverable fluid is reduced.

Accordingly, referring to FIGS. 6A and 6B, fluid channel 60-1 has an interior wall 60-2 that has a plurality of elongate protrusions 60-3 that project toward an interior of the fluid channel 60-1, e.g., generally toward central longitudinal axis 52. In the present embodiment, the plurality of elongate protrusions 60-3 is in the form of a plurality of elongate ribs that extend longitudinally in fluid channel 60-1. Also, as in the present embodiment, the plurality of elongate protrusions 60-3 may extend proximally into opening 48-1 of intermediate wall 48.

A cross-section of fluid channel 60-1 tapers in a direction 71 from filter member 62 toward fluid jetting chip 66. In the present embodiment, interior wall 60-2 of hollow throat portion 60 has a frustoconical shape with the plurality of elongate protrusions 60-3 projecting toward an interior of fluid channel 60-1.

To effect assembly of fluidic dispensing apparatus 10, as depicted in FIG. 1, from the unassembled state depicted in FIG. 2, fluid dispensing cartridge 16 is positioned in cartridge housing 14, prior to cartridge housing 14 being connected to controller portion 12. When fluid dispensing cartridge 16 is installed in cartridge housing 14, hollow throat portion 60 of fluid dispensing cartridge 16 extends distally through distal opening 14-6 of cartridge housing 14. Cartridge housing 14 is then connected to controller portion 12 to form handle 10-1, which in turn establishes electrical connections between the plurality of electrical contacts 30 of controller portion 12 and the plurality of electrical contacts 68 of fluid dispensing cartridge 16.

Referring to FIGS. 1-4, optionally, fluid dispensing cartridge 16 may include cartridge throat cover 18. In the present embodiment, cartridge throat cover 18 may be installed on fluid dispensing cartridge 16 to cover hollow throat portion 60, either before or after fluid dispensing cartridge 16 is installed in handle 10-1, since the largest diameter of cartridge throat cover 18 is smaller than the diameter of distal opening 14-6 of cartridge housing 14.

Depending on the use application, cartridge throat cover 18 may be either of a single use component, or a multiple use component. For example, in a medicinal delivery application, cartridge throat cover 18 may be disposed of and replaced, such as for sanitary reasons. Alternatively, cartridge throat cover 18 may be removed and cleaned, such as by immersing cartridge throat cover 18 in a sanitizing solution, and then reinstalled.

Figure 7A:
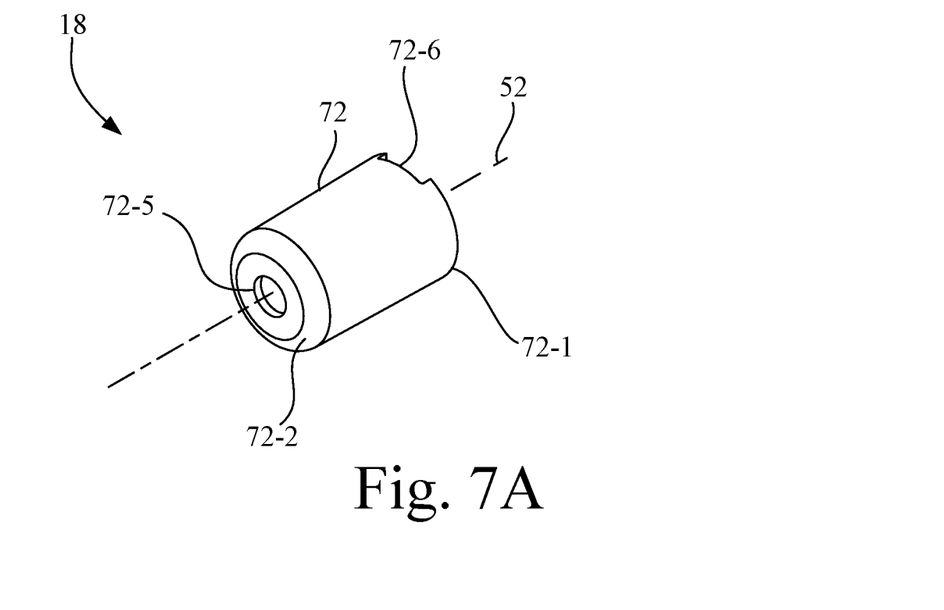
FIG. 7A is an enlarged predominantly rear perspective view of the cartridge throat cover of the fluidic dispensing apparatus of FIGS. 1-4.
Figure 7B:
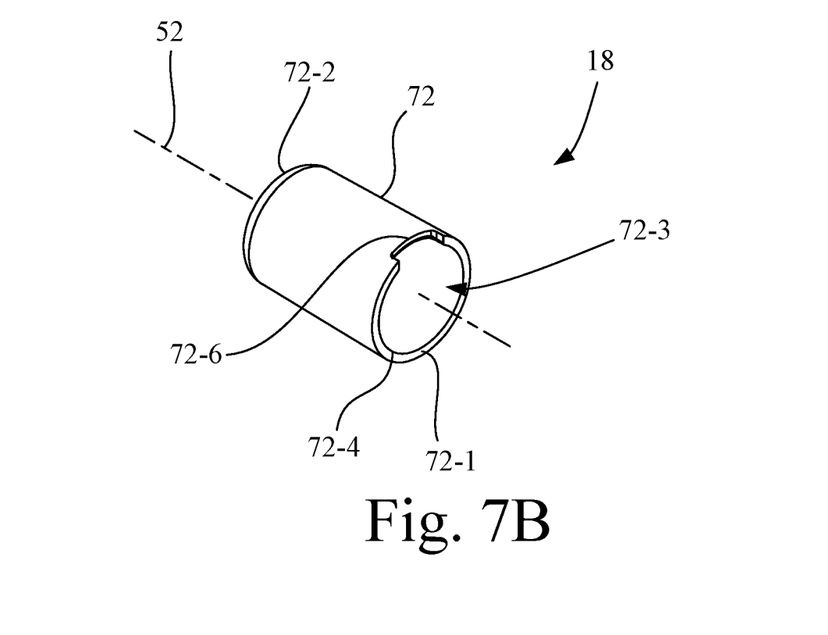
FIG. 7B is an enlarged predominantly front perspective view of the cartridge throat cover of FIG. 7A.

Referring also to FIGS. 7A and 7B, cartridge throat cover 18 has a cover body 72 having a first end 72-1, a second end 72-2, and an internal cavity 72-3 that extends between first end 72-1 and second end 72-2. First end 72-1 has a cover opening 72-4. Each of cover opening 72-4 of first end 72-1 and internal cavity 72-3 has a size and shape that accommodates hollow throat portion 60 of housing body 44. In other words, each of cover opening 72-4 and internal cavity 72-3 is sized and shaped to be removably received over hollow throat portion 60 of housing body 44. Second end 72-2 of cover body 72 has a nozzle opening 72-5.

Cover body 72 includes mounting features 72-6, e.g., a recess for clearance to circuit trace 70, to establish a detachable connection with fluid dispensing cartridge 16 when cartridge throat cover 18 is installed over hollow throat portion 60 of housing body 44 of fluid dispensing cartridge 16.

Alternatively, it is contemplated that cartridge throat cover 18 may be formed integral with cartridge housing 14 as a single-piece component. In this alternative, depending on the use application, cartridge housing 14 having cartridge throat cover 18 may be either of a single use component, or a multiple use component. For example, in a medicinal delivery application, cartridge housing 14 having cartridge throat cover 18 may be disposed of and replaced, such as for sanitary reasons. Alternatively, cartridge housing 14 having cartridge throat cover 18 may be removed and cleaned, such as by immersing cartridge housing 14 having cartridge throat cover 18 in a sanitizing solution, and then reinstalled.

Figure 8A:
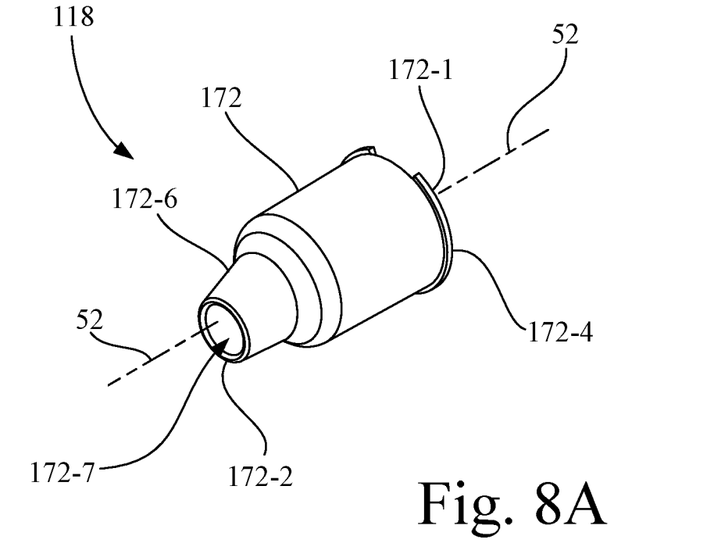
FIG. 8A is an enlarged predominantly rear perspective view of an alternative cartridge throat cover for use with the fluid dispensing cartridge of the fluidic dispensing apparatus of FIGS. 1-4.
Figure 8B:
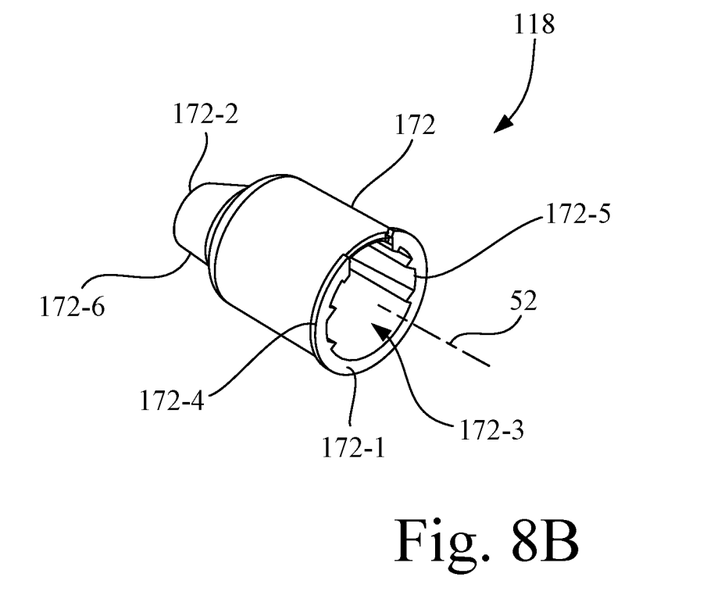
FIG. 8B is an enlarged predominantly front perspective view of the alternative cartridge throat cover of FIG. 8A.

FIGS. 8A and 8B depict another embodiment of a cartridge throat cover 118 suitable for use with fluid dispensing cartridge 16, and is a substitute for cartridge throat cover 18 depicted in FIGS. 1-4. Cartridge throat cover 118 has a cover body 172 having a first end 172-1, a second end 172-2, and an internal cavity 172-3 that extends between first end 172-1 and second end 172-2.

In the embodiment of FIGS. 8A and 8B, first end 172-1 includes an annular lip 172-4 that projects radially in a direction away from central longitudinal axis 52. In addition, first end 172-1 of cartridge throat cover 118 has a cover opening 172-5. Each of cover opening 172-5 of first end 172-1 and internal cavity 172-3 has a size and shape that accommodates hollow throat portion 60 of housing body 44 of fluid dispensing cartridge 16.

In the present embodiment, annular lip 172-4 serves as a mounting feature. In particular, referring to FIGS. 2 and 4 in relation to FIGS. 8A and 8B, annular lip 172-4 is sized and shaped so as to annularly engage interior tapered annular surface 14-7 when cartridge throat cover 118 is inserted into proximal opening 14-5 of cartridge housing 14. As such, in the embodiment of FIGS. 8A and 8B, cartridge throat cover 118 is positioned over hollow throat portion 60 of fluid dispensing cartridge 16 prior to cartridge housing 14 being connected to controller portion 12. In turn, annular lip 172-4 is wedged between interior tapered annular surface 14-7 of cartridge housing 14 and intermediate wall 48 of housing body 44 of fluid dispensing cartridge 16 when cartridge housing 14 is connected to controller portion 12.

Referring again to FIGS. 8A and 8B, cover body 172 has a nozzle portion 172-6 that is proximal to second end 172-2. Nozzle portion 172-6 has a nozzle opening 172-7 located at second end 172-2. In the present embodiment, nozzle portion 172-6 is an angled nozzle portion that positions nozzle opening 172-7 to direct the jetted fluid from fluid jetting chip 66 of fluid dispensing cartridge 16 (see FIGS. 2 and 4) in a direction away from central longitudinal axis 52, and likewise, away from longitudinal axis 20 of fluidic dispensing apparatus 10.

Thus, it can be seen that multiple types and configurations of the cartridge throat cover may be realized, so that customization of fluidic dispensing apparatus 10 is very easy and inexpensive, and accommodates various use applications.

Figure 9:
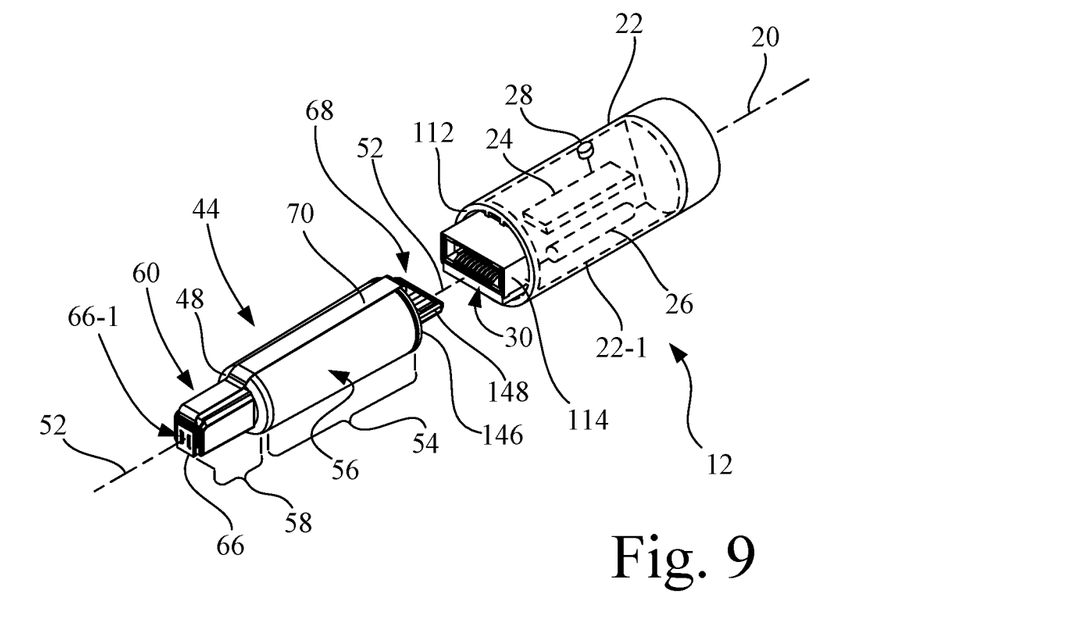
FIG. 9 is a predominantly rear perspective view depicting an alternative electrical connection arrangement for the controller portion and the fluid dispensing cartridge of the fluidic dispensing apparatus of FIGS. 1-4.
Figure 10:
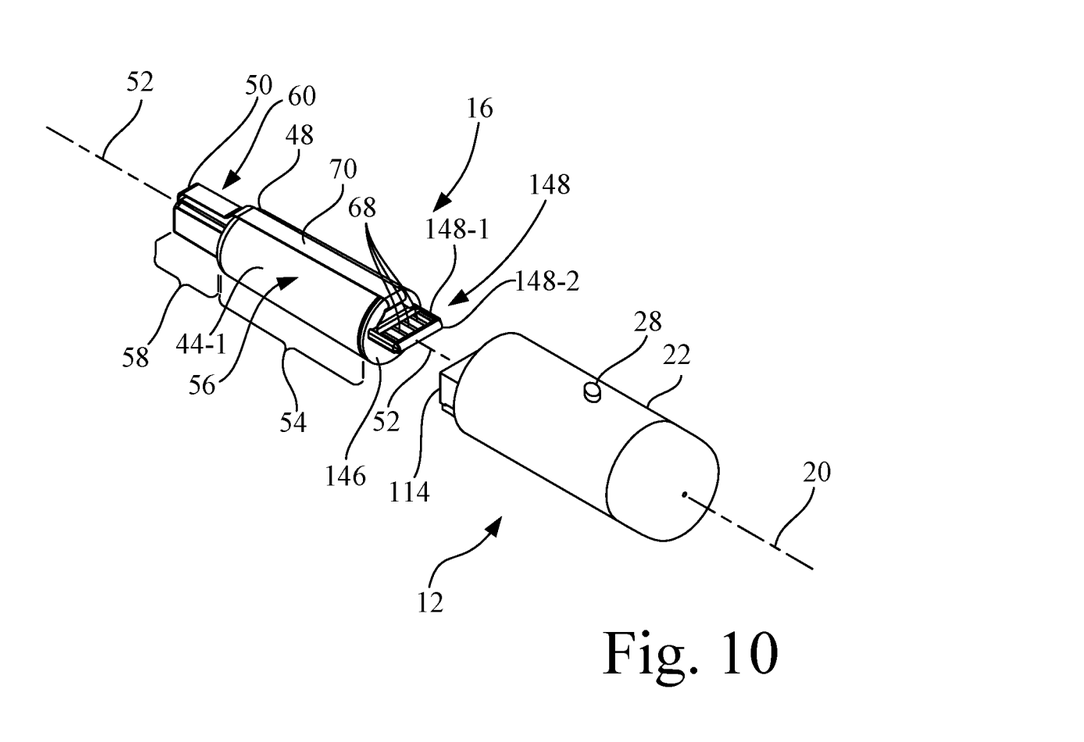
FIG. 10 is a predominantly front perspective view depicting the alternative electrical connection arrangement of the controller portion and the fluid dispensing cartridge of FIG. 9.

FIGS. 9 and 10 depict an alternative electrical connection of controller portion 12 and fluid dispensing cartridge 16. In particular, the plurality of electrical contacts 30 of controller portion 12 and the plurality of electrical contacts 68 of fluid dispensing cartridge 16 may be arranged to facilitate an edge connection, rather than an end connection. In this embodiment, cartridge housing 14 and/or cartridge throat covers 18, 118 may be optional.

In this alternative embodiment, a distal end portion 112 of controller portion 12 includes a socket portion 114 that includes a parallel arrangement of the plurality of electrical contacts 30. Also, in this alternative embodiment, fluid dispensing cartridge 16 is fitted with a proximal end wall 146 connected to body region 54, as a substitute for proximal end wall 46 of the previous embodiments. Proximal end wall 146 has a mounting projection 148 that extends proximally from the proximal end wall 146. Mounting projection 148 is sized and shaped to be slidably received in socket portion 114 of controller portion 12 in a snug fit. In the present embodiment, each of the mounting projection 148 and fluid jetting chip 66 is located on central longitudinal axis 52.

Referring to FIG. 10, mounting projection 148 defines a first projection surface 148-1 and a second projection surface 148-2. The plurality of electrical contacts 68 may extend longitudinally, e.g., in parallel, along at least one of the first projection surface 148-1 and second projection surface 148-2 for engagement with the plurality of electrical contacts 30 of controller portion 12 when mounting projection 148 of this alternative embodiment of fluid dispensing cartridge 16 is slidably received in mounting engagement with socket portion 114 of controller portion 12.

As used herein, "substantially," "generally," and other words of degree are relative modifiers intended to indicate permissible variation from the characteristic so modified.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A fluid dispensing cartridge, comprising:
a housing body having a proximal end wall, a distal end wall in parallel with the proximal end wall, a fluid chamber, and a hollow throat portion, the fluid chamber being in fluid communication with the hollow throat portion, the proximal end wall providing a proximal termination of the fluid chamber and the distal end wall providing a distal termination of the hollow throat portion;
a plurality of electrical contacts that face proximally from the proximal end wall; and
a fluid jetting chip having a plurality of fluid jetting nozzles.

2. The fluid dispensing cartridge of claim 1, wherein the plurality of electrical contacts are distributed on the proximal end wall.

3. The fluid dispensing cartridge of claim 2, wherein at least a portion of the plurality of electrical contacts are arranged in a circular pattern that projects from the proximal end wall.

4. The fluid dispensing cartridge of claim 1, comprising a mounting projection that extends proximally from the proximal end wall, the mounting projection defining a first projection surface and a second projection surface, and wherein the plurality of electrical contacts extend longitudinally along at least one of the first projection surface and the second projection surface.

5. The fluid dispensing cartridge of claim 4, wherein the fluid dispensing cartridge has a central longitudinal axis, and wherein each of the mounting projection and the fluid jetting chip are located on the central longitudinal axis.

6. The fluid dispensing cartridge of claim 1, wherein the housing body has an exterior surface, and further comprising a circuit trace, the circuit trace being electrically connected to the plurality of electrical contacts projecting proximally from the proximal end wall and the circuit trace being electrically connected to the fluid jetting chip, wherein the circuit trace extends from the proximal end wall to the distal end wall along the exterior surface of the housing body and is attached to the exterior surface.

7. The fluid dispensing cartridge of claim 1, wherein the proximal end wall has a first surface area and distal end wall has a second surface area, the first surface area being greater than the second surface area.

8. The fluid dispensing cartridge of claim 1, wherein the hollow throat portion defines a fluid channel having a length that, in part, defines a separation distance between the fluid jetting chip and the plurality of electrical contacts.

9. The fluid dispensing cartridge of claim 1, wherein the fluid dispensing cartridge has a central longitudinal axis, and wherein a center of each of the proximal end wall from which the plurality of electrical contacts project face, and the fluid jetting chip, are located on the central longitudinal axis.

10. The fluid dispensing cartridge of claim 1, wherein the distal end wall is positioned at one longitudinal end of the housing body and the proximal end wall is positioned at another longitudinal end of the housing body.

11. A fluidic dispensing apparatus, comprising:
a handle having a controller portion and a cartridge housing, the controller portion having a first plurality of electrical contacts, the housing being removably engaged with the controller portion, the cartridge housing having a distal opening;
a fluid dispensing cartridge positioned in the cartridge housing, the fluid dispensing cartridge having a proximal end wall and a hollow throat portion that extends distally through the distal opening, the hollow throat portion having a distal end wall that mounts a fluid jetting chip, the fluid jetting chip having a plurality of fluid jetting nozzles, and having a second plurality of electrical contacts that face proximally from the proximal end wall for engagement with the first plurality of electrical contacts of the controller portion.

12. The fluidic dispensing apparatus of claim 11, wherein the second plurality of electrical contacts are distributed on the proximal end wall.

13. The fluidic dispensing apparatus of claim 12, wherein at least a portion of the second plurality of electrical contacts are arranged in a circular pattern that projects from the proximal end wall.

14. The fluidic dispensing apparatus of claim 11, comprising a mounting projection that extends proximally from the proximal end wall, the mounting projection defining a first projection surface and a second projection surface, and wherein the second plurality of electrical contacts extend longitudinally along at least one of the first projection surface and the second projection surface.

15. The fluidic dispensing apparatus of claim 11, wherein the fluid dispensing cartridge has a central longitudinal axis, and wherein each of the mounting projection and the fluid jetting chip are located on the central longitudinal axis.

16. The fluidic dispensing apparatus of claim 11, wherein the housing body has an exterior surface, and further comprising a circuit trace, the circuit trace being electrically connected to the second plurality of electrical contacts projecting proximally from the proximal end wall and the circuit trace being electrically connected to the fluid jetting chip, wherein the circuit trace extends from the proximal end wall to the distal end wall along the exterior surface of the housing body and is attached to the exterior surface.

17. The fluidic dispensing apparatus of claim 11, wherein the proximal end wall has a first surface area and distal end wall has a second surface area, the first surface area being greater than the second surface area.

18. The fluidic dispensing apparatus of claim 11, wherein the hollow throat portion defines a fluid channel having a length that, in part, defines a separation distance between the fluid jetting chip and the second plurality of electrical contacts.

19. The fluidic dispensing apparatus of claim 11, wherein the fluid dispensing cartridge has a central longitudinal axis, and wherein a center of each of the proximal end wall from which the second plurality of electrical contacts face proximally, and the fluid jetting chip, are located on the central longitudinal axis.

* * * * *